United States Patent
Parker et al.

(10) Patent No.: US 8,150,083 B2
(45) Date of Patent: Apr. 3, 2012

(54) PIEZOELECTRIC BONE CONDUCTION DEVICE HAVING ENHANCED TRANSDUCER STROKE

(75) Inventors: John Parker, Roseville (AU); Hans Jaeger, Thunstetten (CH); Christian M. Peclat, Neuchatel (CH)

(73) Assignee: Cochlear Limited, Macquarie University, NSW (AU)

( * ) Notice: Subject to any disclaimer, the term of this patent is extended or adjusted under 35 U.S.C. 154(b) by 924 days.

(21) Appl. No.: 12/168,529

(22) Filed: Jul. 7, 2008

(65) Prior Publication Data

US 2009/0245555 A1 Oct. 1, 2009

Related U.S. Application Data

(60) Provisional application No. 61/041,185, filed on Mar. 31, 2008.

(51) Int. Cl.
  *H04R 25/00* (2006.01)
(52) U.S. Cl. ...................................... 381/326; 29/896.21
(58) Field of Classification Search ................ 29/896.21; 381/326
  See application file for complete search history.

(56) References Cited

U.S. PATENT DOCUMENTS

| | | | |
|---|---|---|---|
| 2,045,403 A | 6/1936 | Nicholides | |
| 2,045,404 A | 6/1936 | Nicholides | |
| 2,045,427 A | 6/1936 | White | |
| 2,239,550 A | 4/1941 | Cubert | |
| 3,594,514 A | 7/1971 | Wingrove | |
| 4,498,461 A | 2/1985 | Hakansson | |
| 4,612,915 A * | 9/1986 | Hough et al. | 600/25 |
| 4,904,233 A | 2/1990 | Hankansson et al. | |
| 4,937,489 A | 6/1990 | Hattori et al. | |
| 4,952,835 A | 8/1990 | Stahlhuth | |
| 4,964,106 A | 10/1990 | Bromfield | |
| 5,228,092 A * | 7/1993 | Nakamura et al. | 381/151 |
| 5,245,245 A | 9/1993 | Goldenberg | |
| 5,286,199 A | 2/1994 | Kipke | |
| 5,444,324 A | 8/1995 | Priest et al. | |
| 5,589,725 A | 12/1996 | Haertling | |
| 5,772,575 A | 6/1998 | Lesinski et al. | |
| 5,788,711 A | 8/1998 | Lehner et al. | |
| 6,273,681 B1 | 8/2001 | Yamakawa et al. | |

(Continued)

FOREIGN PATENT DOCUMENTS

DE 19643180 4/1997

(Continued)

OTHER PUBLICATIONS

Piezomechanik GmbH. Piezoelectric bending actuators Disk Translators ("bimorphs") Piezoelectric tubes. pp. 1-12.

(Continued)

*Primary Examiner* — Eugene Lee
(74) *Attorney, Agent, or Firm* — Kilpatrick, Townsend & Stockton, LLP.

(57) ABSTRACT

A bone conduction device for enhancing the hearing of a recipient, comprising a sound input element configured to receive an acoustic sound signal and an electronics module configured generate an electrical signal representing the acoustic sound signal. The device further comprises a piezoelectric transducer comprising at least one piezoelectric element configured to deform along at least one axis in response to an application of the electrical signal thereto, the transducer configured to generate an transducer stroke based on the deformation, the stroke having a magnitude that exceeds the magnitude of the deformation, wherein the transducer stroke is utilized to generate a mechanical force for delivery to the recipient's skull.

27 Claims, 12 Drawing Sheets

U.S. PATENT DOCUMENTS

| | | | |
|---|---|---|---|
| 6,294,859 B1 | 9/2001 | Jaenker | |
| 6,371,415 B1 | 4/2002 | Lorkowski et al. | |
| 6,411,009 B2 | 6/2002 | Jaenker | |
| 6,463,157 B1 | 10/2002 | May | |
| 6,554,761 B1* | 4/2003 | Puria et al. | 600/25 |
| 6,629,922 B1 | 10/2003 | Puria et al. | |
| 6,631,197 B1* | 10/2003 | Taenzer | 381/316 |
| 6,751,334 B2 | 6/2004 | Håkansson | |
| 6,927,528 B2 | 8/2005 | Barillot et al. | |
| 6,994,110 B2 | 2/2006 | Barillot et al. | |
| 7,026,746 B2 | 4/2006 | Audren et al. | |
| 7,045,932 B2 | 5/2006 | Xu et al. | |
| 7,224,815 B2 | 5/2007 | Maltan et al. | |
| 7,378,783 B2 | 5/2008 | Pelrine et al. | |
| 7,564,988 B2* | 7/2009 | Azima et al. | 381/326 |
| 7,722,524 B2 | 5/2010 | Lupin et al. | |
| 2002/0039427 A1* | 4/2002 | Whitwell et al. | 381/312 |
| 2003/0137218 A1 | 7/2003 | Hermle et al. | |
| 2005/0020873 A1 | 1/2005 | Berrang et al. | |
| 2006/0023908 A1* | 2/2006 | Perkins et al. | 381/328 |
| 2006/0025648 A1 | 2/2006 | Lupin et al. | |
| 2007/0041595 A1 | 2/2007 | Carazo et al. | |
| 2007/0156011 A1 | 7/2007 | Westerkull | |
| 2007/0191673 A1 | 8/2007 | Ball et al. | |
| 2009/0052698 A1* | 2/2009 | Rader et al. | 381/151 |
| 2009/0115292 A1 | 5/2009 | Ueda et al. | |
| 2009/0245553 A1 | 10/2009 | Parker | |
| 2009/0245555 A1 | 10/2009 | Parker et al. | |
| 2009/0247810 A1 | 10/2009 | Parker et al. | |
| 2009/0247811 A1 | 10/2009 | Parker | |
| 2009/0248085 A1 | 10/2009 | Parker | |
| 2009/0248086 A1 | 10/2009 | Parker | |
| 2010/0179375 A1 | 7/2010 | Andersson | |
| 2010/0298626 A1 | 11/2010 | Andersson et al. | |

FOREIGN PATENT DOCUMENTS

| | | |
|---|---|---|
| JP | 59-178986 A | 10/1984 |
| JP | 64-073781 A | 3/1989 |
| JP | 01-290272 A | 11/1989 |
| WO | WO 01/93633 A1 | 12/2001 |
| WO | WO 01/93634 A1 | 12/2001 |
| WO | WO 01/93635 A1 | 12/2001 |
| WO | 03001846 | 1/2003 |
| WO | WO 03/096744 A1 | 11/2003 |
| WO | WO 2004/032566 A1 | 4/2004 |
| WO | WO 2007/024657 A2 | 3/2007 |
| WO | WO 2007/052251 A2 | 5/2007 |
| WO | WO 2008/143573 A1 | 11/2008 |
| WO | WO 2009/121104 A1 | 10/2009 |
| WO | WO 2009/121116 A9 | 11/2009 |

OTHER PUBLICATIONS

Janocha, "Actuators: Basics and Applications", Springer Verlag 2004, Jul. 8, 2009, pp. 265-267. Available at: <http://books.google.com.au/books?id.

Juuti, et al., "Mechanically Amplified large displacement piezoelectric actuators", Sensors and Actuators A 120, Dec. 22, 2004, pp. 225-231.

International Application No. PCT/AU2009/000358, International Preliminary Report on Patentability mailed on Oct. 5, 2010, 7 Pages.

International Application No. PCT/AU2009/000358, International Search Report mailed on Jul. 14, 2009, 4 Pages.

International Application No. PCT/AU2009/000358, Written Opinion mailed on Jul. 14, 2009, 6 Pages.

International Application No. PCT/AU2009/000372, International Preliminary Report on Patentability mailed on Oct. 5, 2010, 8 Pages.

International Application No. PCT/AU2009/000372, International Search Report mailed on Jun. 29, 2009, 3 Pages.

International Application No. PCT/AU2009/000372, Written Opinion mailed on Jun. 29, 2009, 7 Pages.

International Application No. PCT/SE2008/000336, International Search Report mailed on Sep. 3, 2008, 4 Pages.

Zhou, et al., "Analysis of a diamond-shaped mechanical amplifier for a piezo actuator", Int J Adv Manuf Technol, vol. 32, 2007, pp. 1-7.

Piezomechanik GMBH, "Piezoelectric bending actuators, Disk translators ("bimorphs"), Piezoelectric tubes," Mar. 2002, pp. 1-12.

Sichel, et al. "New Approach for Implantable Hearing Aids: A Feasibility Study" Ann Otol Rhinol Laryngol. 113:2004, pp. 936-940.

Selection guide for piezo actuators. Cedrat Technologies—Piezo Products Catalogue—Version 3.0—Sep. 2003.

* cited by examiner

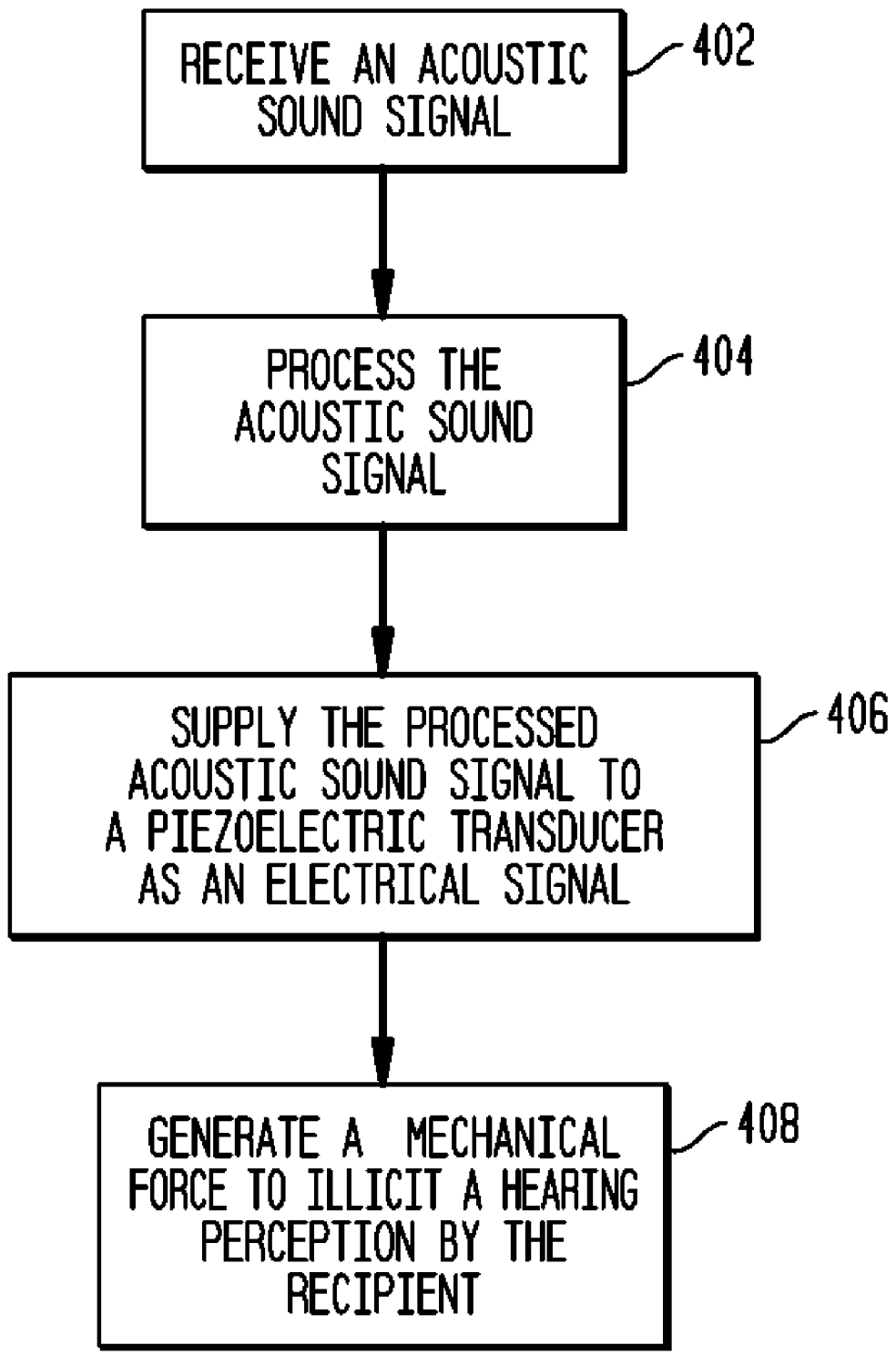

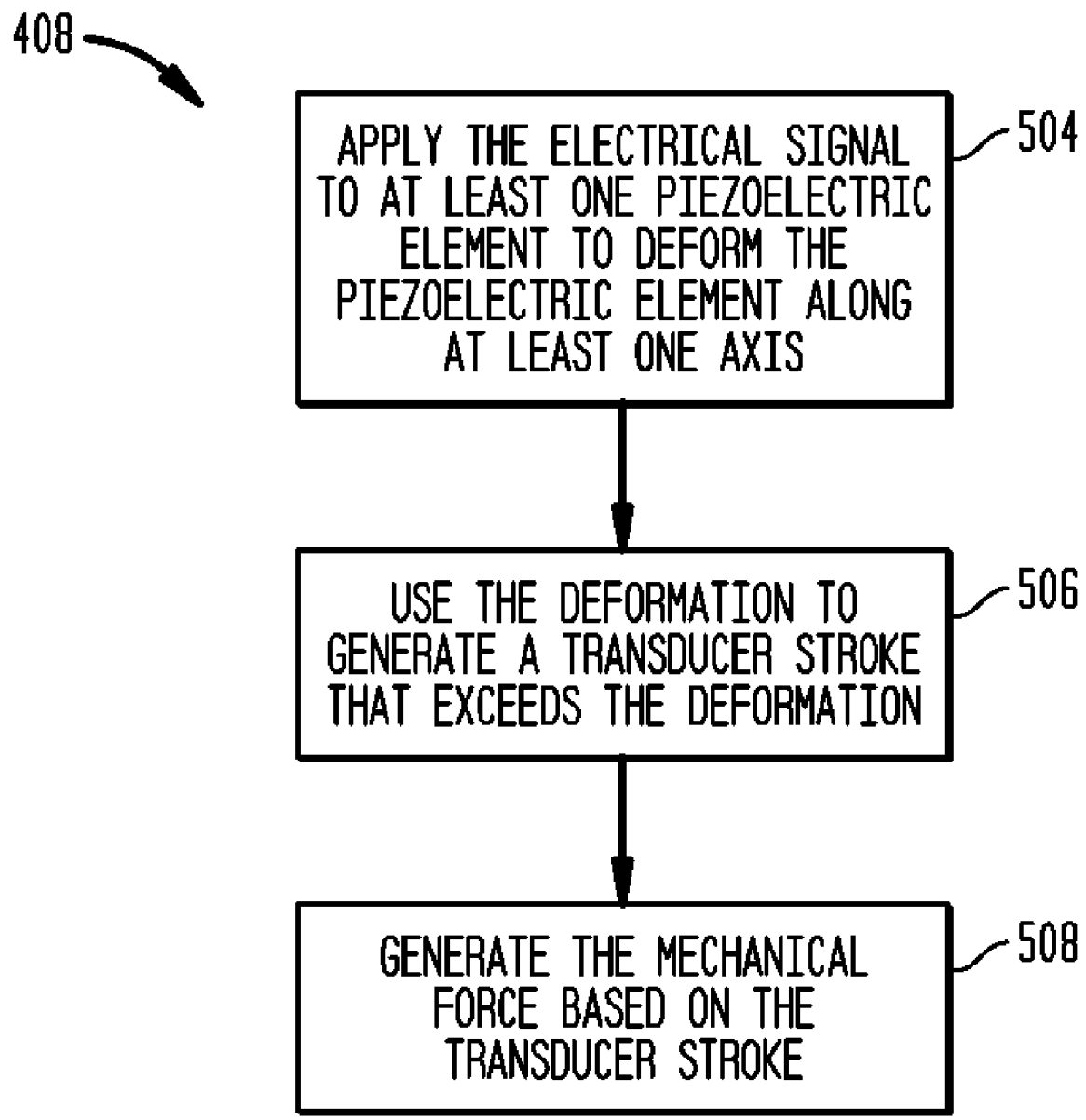

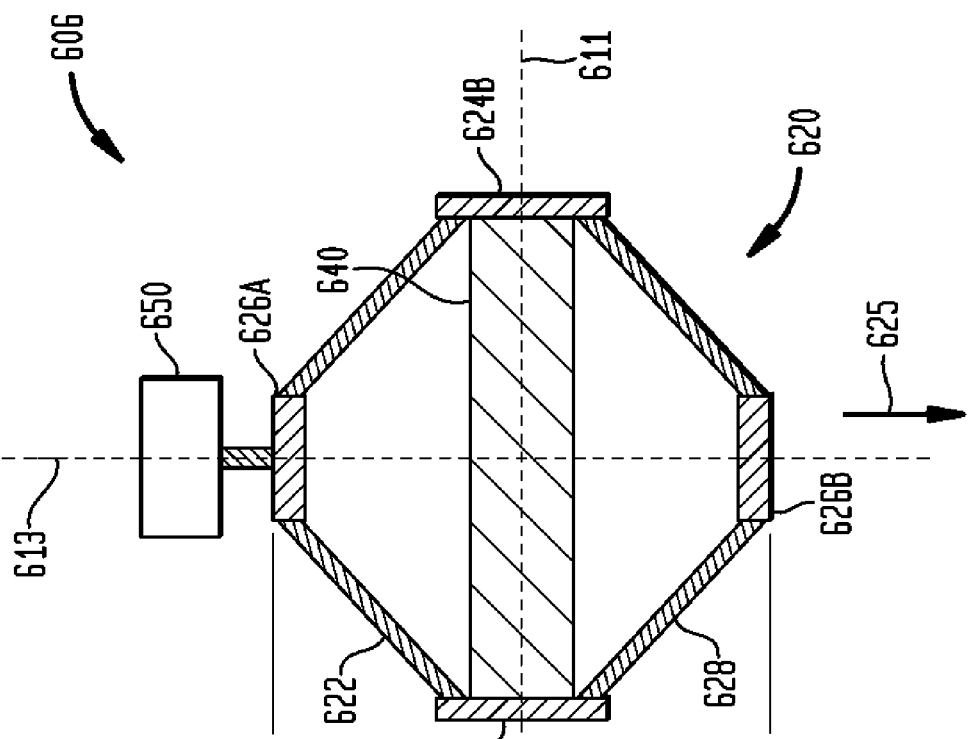
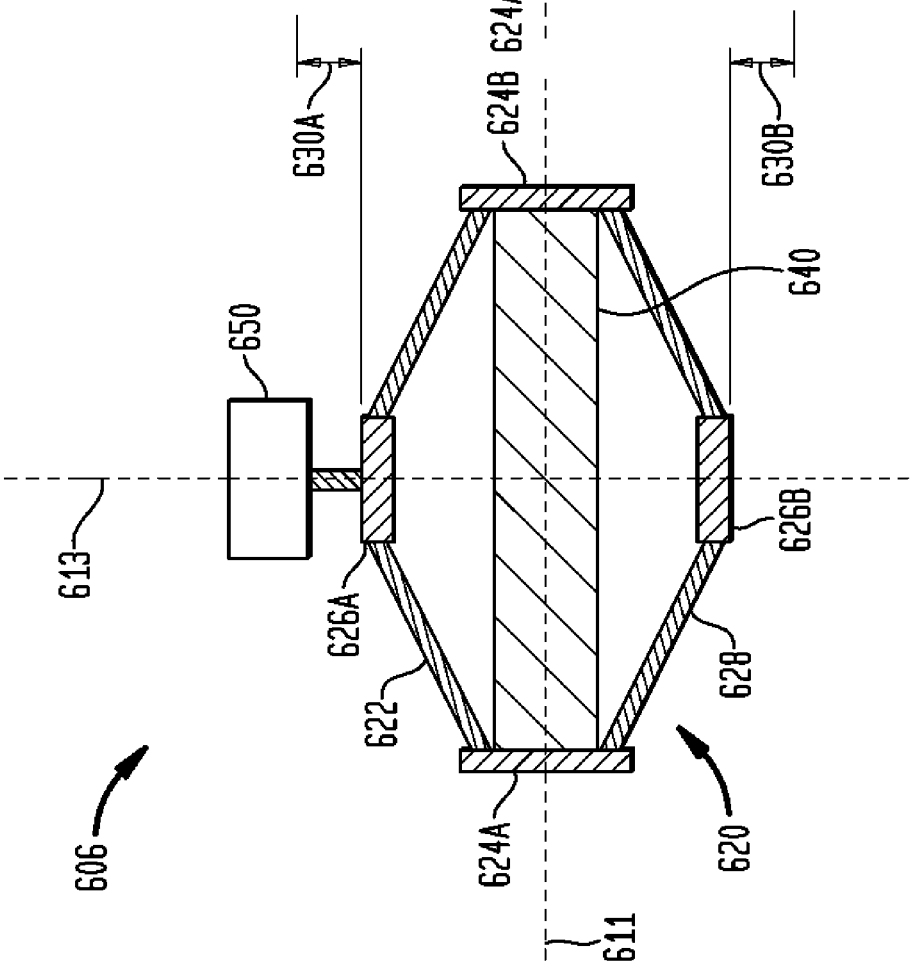

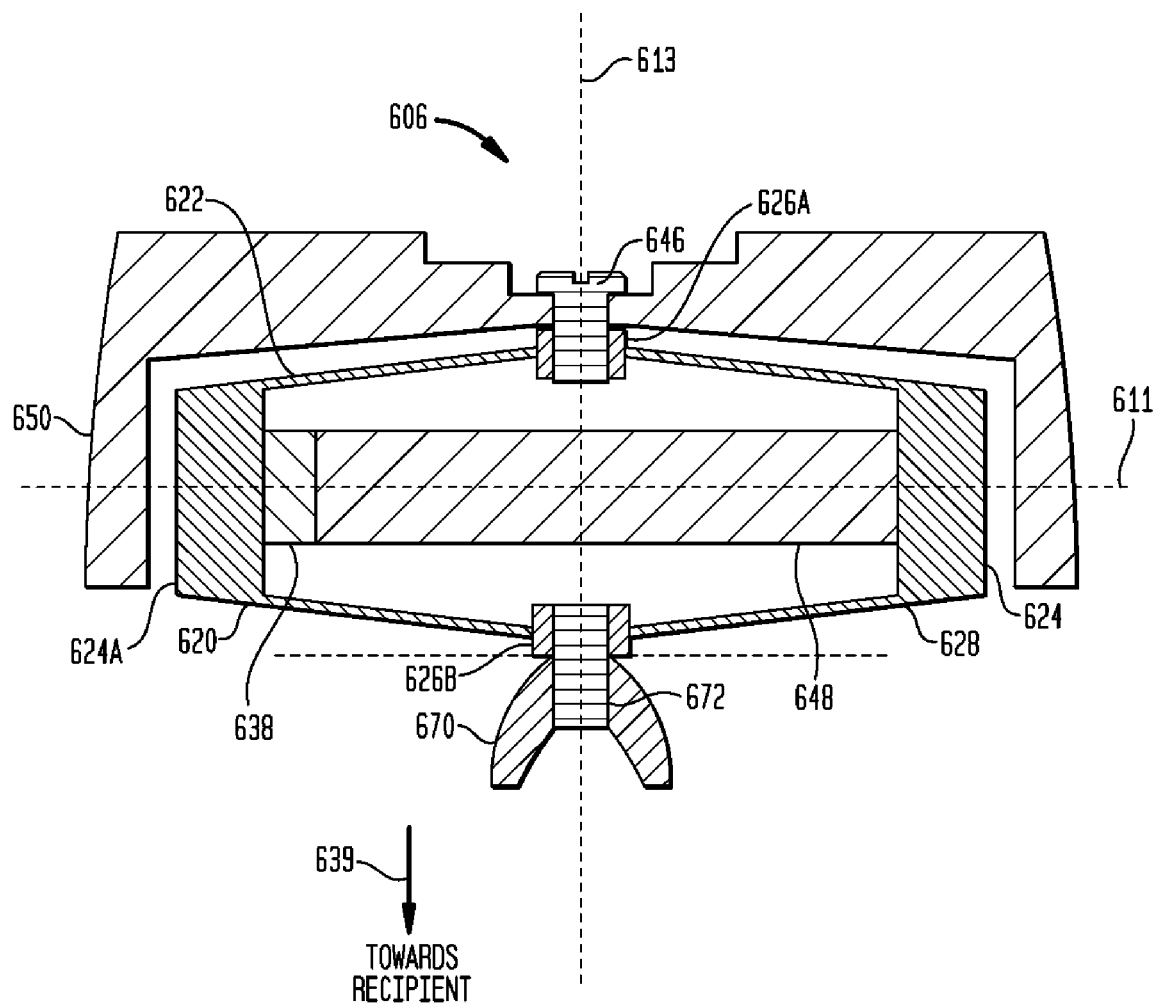

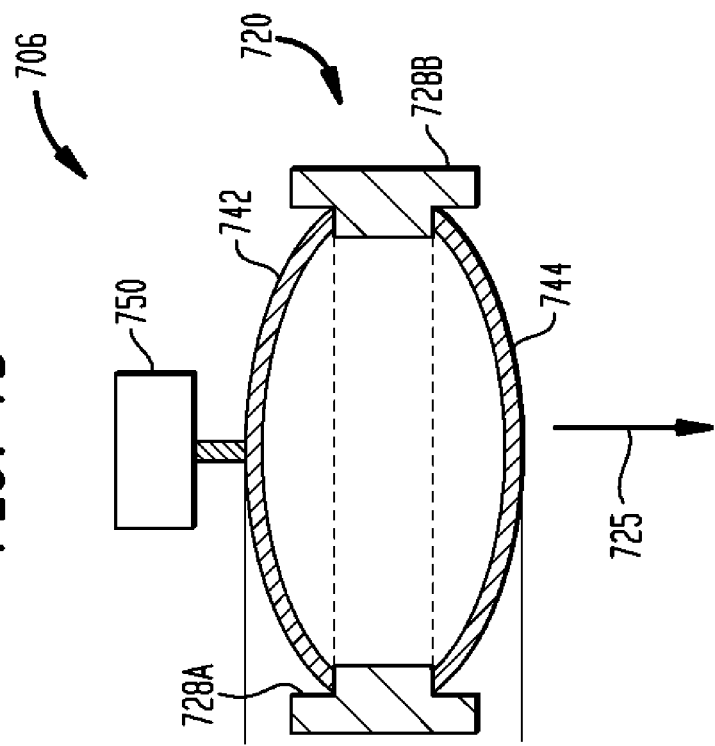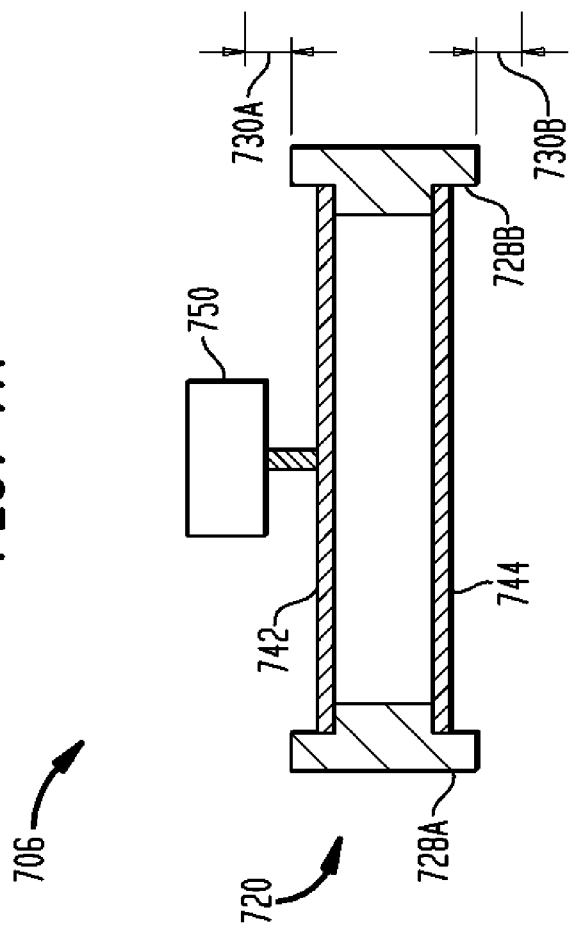

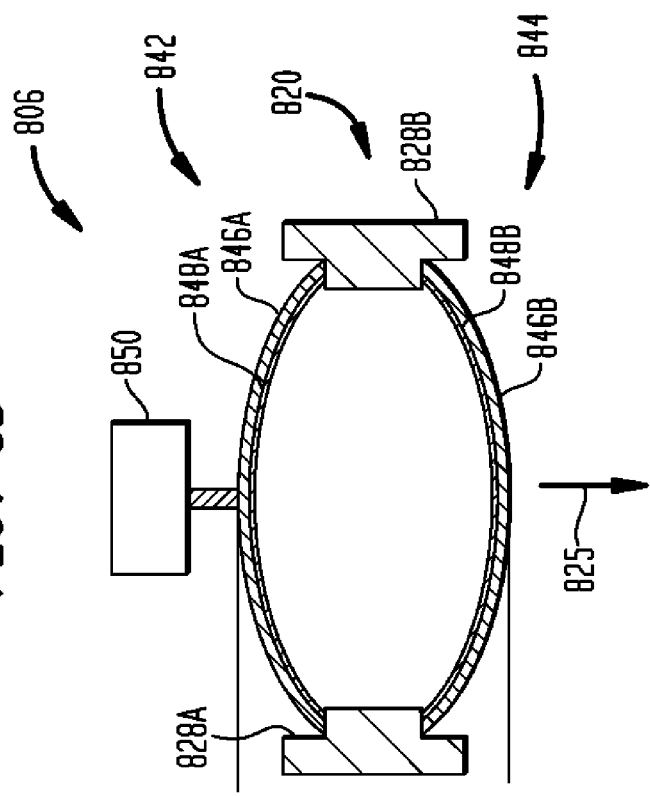
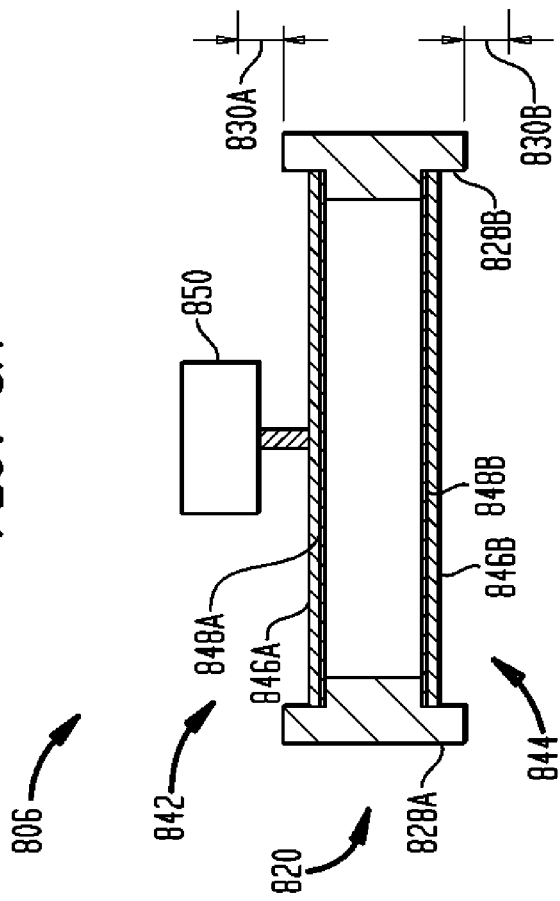

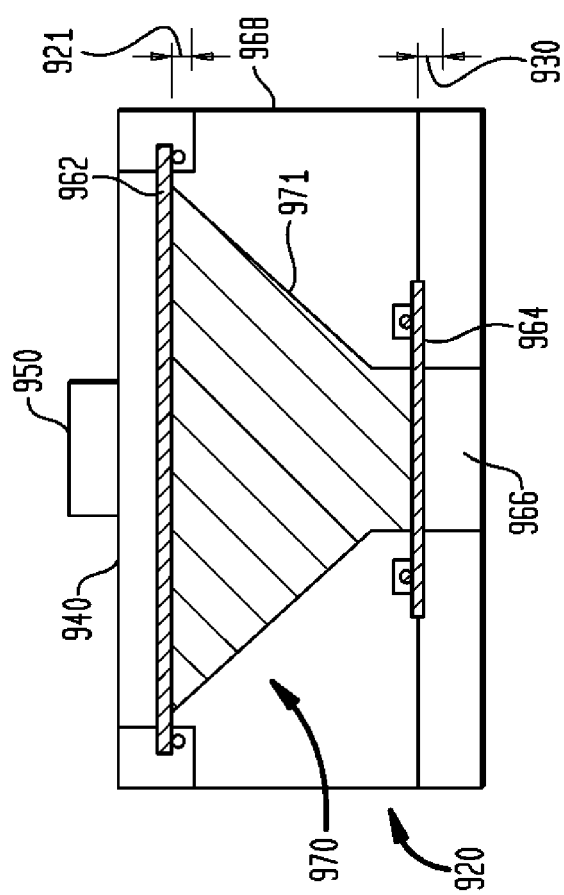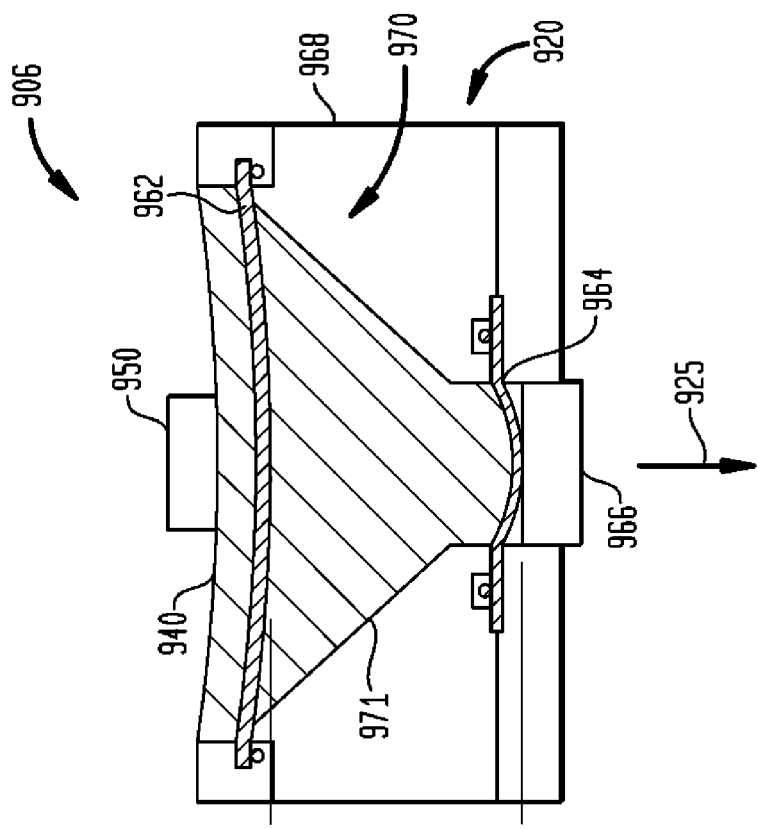

PIEZOELECTRIC BONE CONDUCTION DEVICE HAVING ENHANCED TRANSDUCER STROKE

CROSS-REFERENCE TO RELATED APPLICATIONS

The present application claims the benefit of U.S. Provisional Patent Application 61/041,185; filed Mar. 31, 2008, which is hereby incorporated by reference herein.

BACKGROUND

1. Field of the Invention

The present invention is generally directed to a bone conduction device, and more particularly, to a piezoelectric bone conduction device having enhanced transducer stroke.

2. Related Art

Hearing loss, which may be due to many different causes, is generally of two types, conductive or sensorineural. In many people who are profoundly deaf, the reason for their deafness is sensorineural hearing loss. This type of hearing loss is due to the absence or destruction of the hair cells in the cochlea which transduce acoustic signals into nerve impulses. Various prosthetic hearing implants have been developed to provide individuals who suffer from sensorineural hearing loss with the ability to perceive sound. One such prosthetic hearing implant is referred to as a cochlear implant. Cochlear implants use an electrode array implanted in the cochlea of a recipient to bypass the mechanisms of the ear. More specifically, an electrical stimulus is provided via the electrode array directly to the cochlea nerve, thereby causing a hearing sensation.

Conductive hearing loss occurs when the normal mechanical pathways to provide sound to hair cells in the cochlea are impeded, for example, by damage to the ossicular chain to ear canal. However, individuals who suffer from conductive hearing loss may still have some form of residual hearing because the hair cells in the cochlea are may remain undamaged.

Individuals who suffer from conductive hearing loss are typically not candidates for a cochlear implant due to the irreversible nature of the cochlear implant. Specifically, insertion of the electrode array into a recipient's cochlea exposes the recipient to risk of the destruction of the majority of hair cells within the cochlea. The destruction of the cochlea hair cells results in the loss of all residual hearing by the recipient.

Rather, individuals suffering from conductive hearing loss typically receive an acoustic hearing aid, referred to as a hearing aid herein. Hearing aids rely on principles of air conduction to transmit acoustic signals through the outer and middle ears to the cochlea. In particular, a hearing aid typically uses an arrangement positioned in the recipient's ear canal to amplify a sound received by the outer ear of the recipient. This amplified sound reaches the cochlea and causes motion of the cochlea fluid and stimulation of the cochlea hair cells.

Unfortunately, not all individuals who suffer from conductive hearing loss are able to derive suitable benefit from hearing aids. For example, some individuals are prone to chronic inflammation or infection of the ear canal and cannot wear hearing aids. Other individuals have malformed or absent outer ear and/or ear canals as a result of a birth defect, or as a result of medical conditions such as Treacher Collins syndrome or Microtia. Furthermore, hearing aids are typically unsuitable for individuals who suffer from single-sided deafness (total hearing loss only in one ear). Cross aids have been developed for single sided deaf individuals. These devices receive the sound from the deaf side with one hearing aid and present this signal (either via a direct electrical connection or wirelessly) to a hearing aid which is worn on the opposite side. The disadvantage of this technology is the need for the individual to wear two hearing aids and suffer the complications of hearing aid use.

When an individual having fully functional hearing receives an input sound, the sound is transmitted to the cochlea via two primary mechanisms: air conduction and bone conduction. As noted above, hearing aids rely primarily on the principles of air conduction. In contrast, other devices, referred to as bone conduction devices, rely predominantly on vibration of the bones of the recipients skull to provide acoustic signals to the cochlea.

Those individuals who cannot derive suitable benefit from hearing aids may benefit from bone conduction devices. Bone conduction devices function by converting a received sound into a mechanical vibration representative of the received sound. This vibration is then transferred to the bone structure of the skull, causing vibration of the recipient's skull. This skull vibration results in motion of the fluid of the cochlea. Hair cells inside the cochlea are responsive to this motion of the cochlea fluid, thereby generate nerve impulses resulting in the perception of the received sound.

A known alternative to a normal air conduction aid is a bone conduction hearing aid which uses a hearing aid to drive a vibrator which is pushed against the skull via a mechanism, such as glasses or wire hoops. These devices are generally uncomfortable to wear and, for some recipients, are incapable of generating sufficient vibration to accurately present certain received sounds to a recipient.

SUMMARY

In one aspect of the invention, a bone conduction device for enhancing the hearing of a recipient is provided. The device comprises: a sound input element configured to receive an acoustic sound signal; an electronics module configured generate an electrical signal representing the acoustic sound signal; and a piezoelectric transducer comprising at least one piezoelectric element configured to deform along at least one axis in response to an application of the electrical signal thereto, the transducer configured to generate a transducer stroke based on the deformation, the transducer stroke having a magnitude that exceeds the magnitude of the deformation, wherein the transducer stroke is utilized to generate a mechanical force for delivery to the recipient's skull.

In a second aspect of the present invention, a method for rehabilitating the hearing of a recipient with a bone conduction device is provided. The method comprises: receiving an electrical representation of an acoustic sound signal; delivering the electrical representation to at least one piezoelectric element of a piezoelectric transducer so as to deform the element; generating, based on the deformation, a transducer stroke having a magnitude that exceeds the magnitude of the deformation; and generating a mechanical force from the transducer stroke, wherein the force is configured for delivery to the recipient's skull.

BRIEF DESCRIPTION OF THE DRAWINGS

Illustrative embodiments of the present invention are described herein with reference to the accompanying drawings, in which:

FIG. 4 is a flowchart illustrating the conversion of an input sound into skull vibration in accordance with embodiments of the present invention;

FIG. 5 is a flowchart illustrating the generation of mechanical skull in accordance with one embodiment of block 408 of FIG. 4;

FIG. 6A is a simplified schematic diagram illustrating embodiments of transducer 306 of FIG. 3;

FIG. 6B is a simplified schematic diagram illustrating embodiments of transducer 306 of FIG. 3;

FIG. 6C is a cross-sectional view of one embodiment of transducer 306 of FIG. 3 along cross-sectional plane 201;

FIG. 7A is a simplified schematic diagram illustrating alternative embodiments of transducer 306 of FIG. 3;

FIG. 7B is a simplified schematic diagram illustrating alternative embodiments of transducer 306 of FIG. 3;

FIG. 8A is a simplified schematic diagram illustrating other embodiments of transducer 306 of FIG. 3;

FIG. 8B is a simplified schematic diagram illustrating other embodiments of transducer 306 of FIG. 3;

FIG. 9A is a simplified schematic diagram illustrating additional embodiments of transducer 306 of FIG. 3; and FIG. 9B is a simplified schematic diagram illustrating additional embodiments of transducer 306 of FIG. 3.

DETAILED DESCRIPTION

Figure 1:
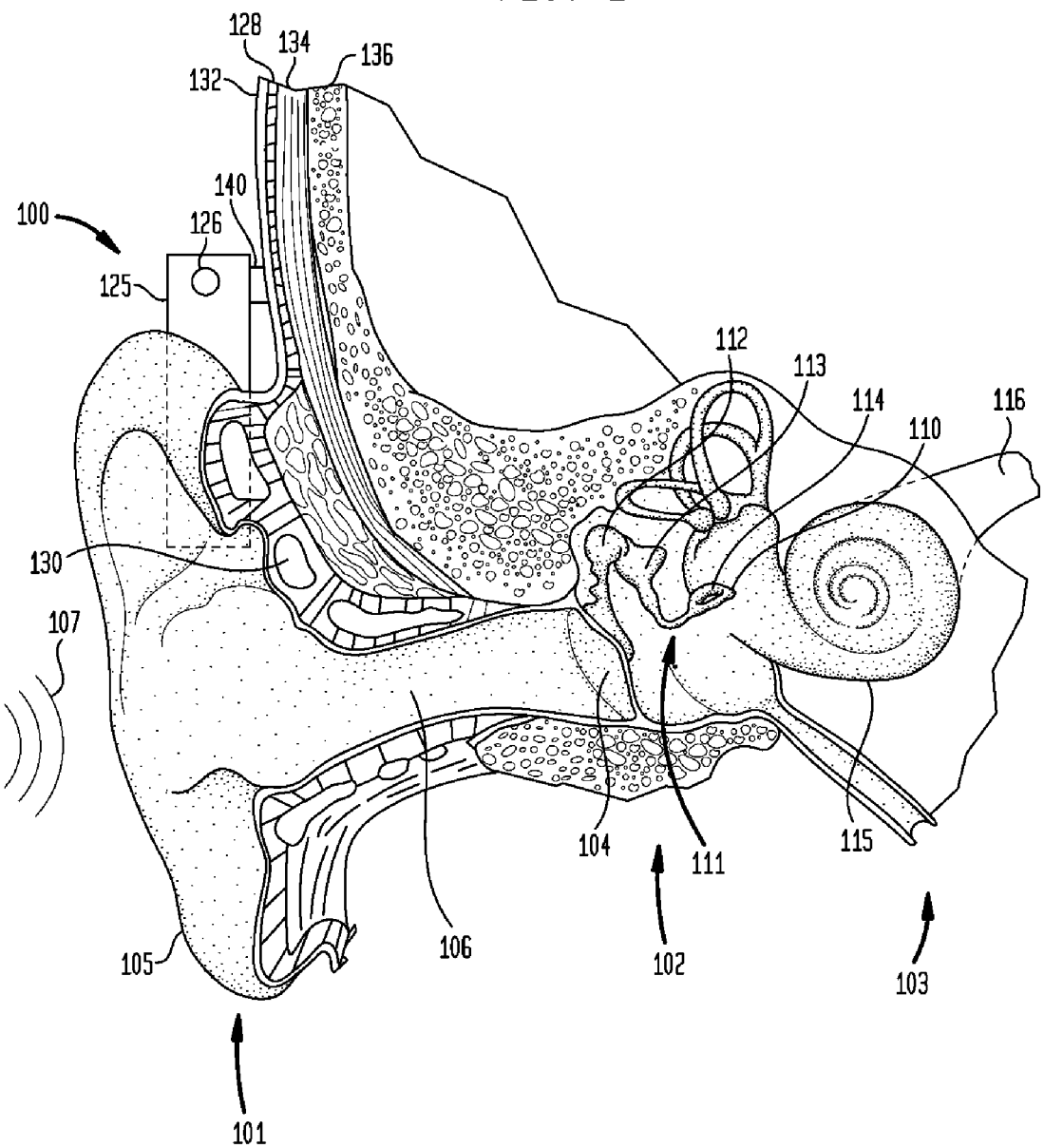
FIG. 1 is a perspective view of an exemplary medical device, namely a bone conduction device, in which embodiments of the present invention may be advantageously implemented.

Embodiments of the present invention are generally directed to a bone conduction device for converting a received acoustic sound signal into a mechanical force for delivery to a recipient's skull. The bone conduction device includes a sound input component, such as microphone, to receive the acoustic sound signal, an electronics module configured to generate an electrical signal representing the acoustic sound signal, and a piezoelectric transducer to convert the electrical signal into a mechanical force for delivery to the recipient's skull. The piezoelectric transducer has a piezoelectric element that deforms in response to application of the electrical signal thereto. The transducer has an output stroke that exceeds the deformation of the piezoelectric element.

The output stroke of the transducer (sometimes referred to herein as the "transducer stroke") is utilized to generate a mechanical force that may be provided to the recipient's skull. The sound perceived by a recipient is dependent, in part, upon the magnitude of mechanical force generated by the transducer. In some bone conduction devices, the magnitude of the mechanical force may be limited by the available transducer stroke. These limitations may cause distortion in the sound signal perceived by the recipient or limit the population of recipient's that may benefit from the device. For example, in certain embodiments, limited transducer stroke results in insufficient gain to adequately represent a received acoustic sound signal for all individuals. This insufficient gain may cause a signal to be clipped or otherwise distorted.

As noted, the piezoelectric transducer comprises a piezoelectric element. The piezoelectric element converts an electrical signal applied thereto into a mechanical deformation (i.e. expansion or contraction) of the element. The amount of deformation of a piezoelectric element in response to an applied electrical signal depends on material properties of the element, orientation of the electric field with respect to the polarization direction of the element, geometry of the element, etc.

The deformation of the piezoelectric element may also be characterized by the free stroke and blocked force of the element. The free stroke of a piezoelectric element refers to the magnitude of deformation induced in the element when a given voltage is applied thereto. Blocked force refers to the force that must be applied to the piezoelectric element to stop all deformation at the given voltage. Generally speaking, piezoelectric elements have a high blocked force, but a low free stroke. In other words, when a voltage is applied to the element, the element will can output a high force, but will only a small stroke.

As noted, bone conduction devices generate a mechanical force that is delivered to the skull, thereby causing motion of the cochlea fluid and a hearing perception by the recipient. In some piezoelectric transducers, the maximum available transducer stroke is equivalent to the free stroke of the piezoelectric element. As such, some bone conduction devices utilizing these types of piezoelectric transducer have a limited transducer stroke and corresponding limits on the magnitude of the mechanical force that may be provided to the skull.

In some embodiments of the present invention, a bone conduction device having a mechanically amplified piezoelectric transducer is provided. In these embodiments, the transducer comprises a mechanical amplifier coupled to a piezoelectric element. When the piezoelectric element deforms, portions of the mechanical amplifier are deflected away from the piezoelectric element. The collective deflection of these portions, which exceeds the deformation of the piezoelectric element, comprises the transducer stroke. In certain embodiments, the mechanical amplifier comprises two endplates coupled to the piezoelectric element, and a pair of opposing hinge arms. When the piezoelectric element deforms, a portion of each of the arms deflect away from the piezoelectric element.

In other embodiments of the present invention, the transducer further comprises a second piezoelectric element. In these embodiments, the first and second piezoelectric elements are positioned substantially parallel and laterally spaced. The first piezoelectric element deforms in a first direction and the second piezoelectric element deforms in the opposite direction from the first element. In these embodiments, the transducer stroke comprises the combined deformation of these piezoelectric elements.

In further embodiments, a hydraulic amplifier is coupled to the piezoelectric element to generate the transducer stroke. The hydraulic amplifier comprises a bounded volume of incompressible fluid, and a first flexible metallic membrane positioned between and adjoining the at least one piezoelectric element and the volume. A second metallic membrane also adjoins the volume approximately opposite to the first membrane. The surface area of the fluid adjoining the second membrane is substantially less than the surface area of the fluid adjoining the first membrane such that a defection of said first membrane is hydraulically amplified and transferred to said second membrane. In these embodiments, when an electrical signal is applied to the piezoelectric element, the first membrane deflects so as to increase the pressure of the volume of fluid. This increased pressure causes a deflection of the second membrane that exceeds the deformation of the piezoelectric element. The deflection of the second membrane comprises the transducer stroke.

FIG. 1 is a perspective view of embodiments of a bone conduction device 100 in which embodiments of the present invention may be advantageously implemented. In a fully functional human hearing anatomy, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 110 through three bones of middle ear 102, collectively referred to as the ossicles 111 and comprising the malleus 112, the incus 113 and the stapes 114. Bones 112, 113 and 114 of middle ear 102 serve to filter and amplify acoustic wave 107, causing oval window 110 to articulate, or vibrate. Such vibration sets up waves of fluid motion within cochlea 115. Such fluid motion, in turn, activates cochlear hair cells (not shown). Cochlear hair cells come in two anatomically and functionally distinct types: the outer and inner hair cells. Activation of one or more types of these hair cells causes appropriate nerve impulses to be transferred through the spiral ganglion cells and auditory nerve 116 to the brain (not shown), where they are perceived as sound.

FIG. 1 also illustrates the positioning of bone conduction device 100 relative to outer ear 101, middle ear 102 and inner ear 103 of a recipient of device 100. As shown, bone conduction device 100 may be positioned behind outer ear 101 of the recipient.

In the embodiments illustrated in FIG. 1, bone conduction device 100 comprises a housing 125 having a microphone 126 positioned therein or thereon. Housing 125 is coupled to the body of the recipient via coupling 140. As described below, bone conduction device 100 may comprise a sound processor, a transducer, transducer drive components and/or various other electronic circuits/devices.

In accordance with embodiments of the present invention, an anchor system (not shown) may be implanted in the recipient. As described below, the anchor system may be fixed to bone 136. In various embodiments, the anchor system may be implanted under skin 132 within muscle 134 and/or fat 128. In certain embodiments, a coupling 140 attaches device 100 to the anchor system.

Figure 2A:
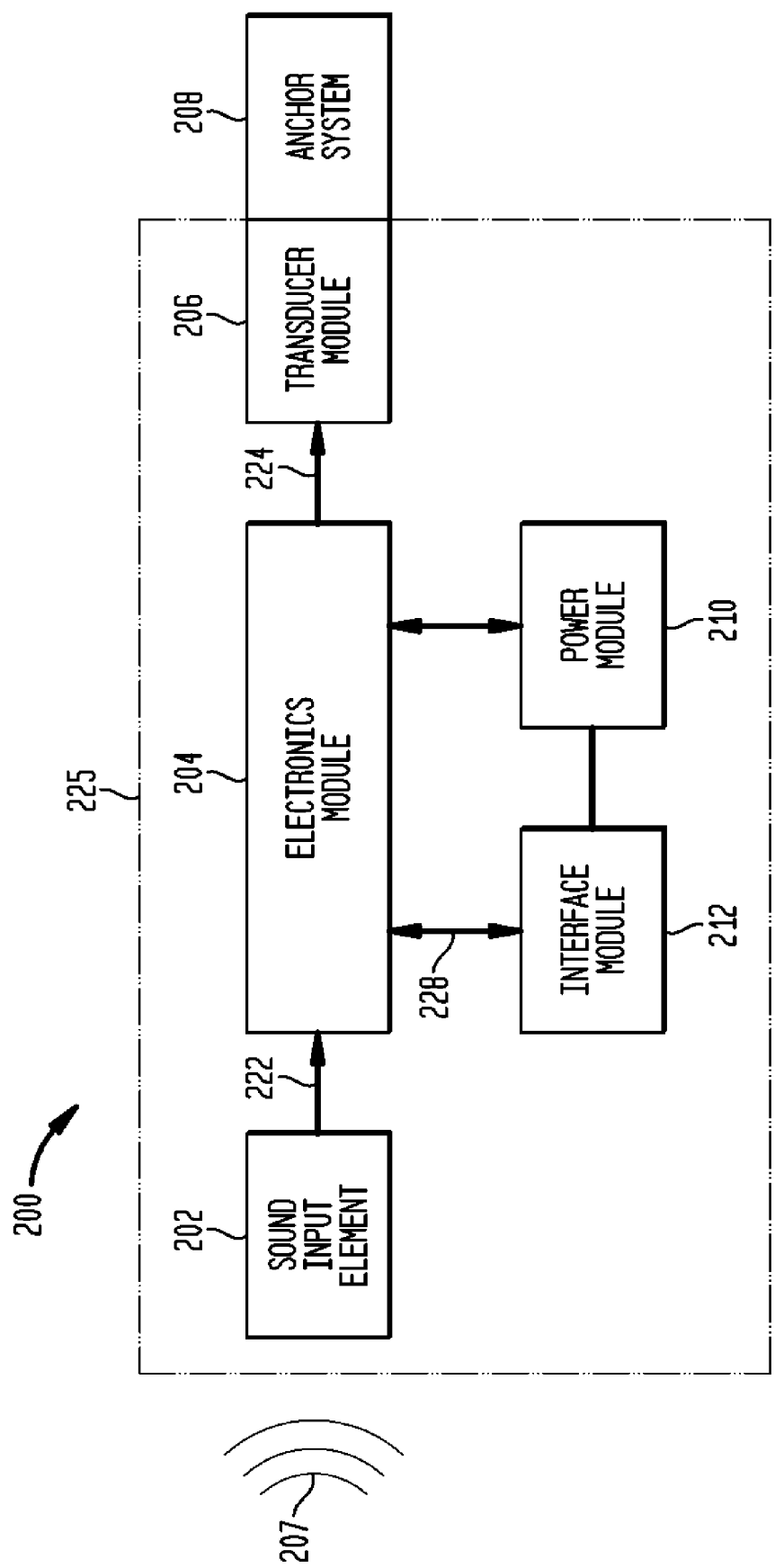
FIG. 2A is a high-level functional block diagram of a bone conduction device, such as the bone conduction device of FIG. 1.

A functional block diagram of one embodiment of bone conduction 100, referred to as bone conduction device 200, is shown in FIG. 2A. In the illustrated embodiment, a sound 207 is received by a sound input element 202. In some embodiments, sound input element 202 is a microphone configured to receive sound 207, and to convert sound 207 into an electrical signal 222. As described below, in other embodiments sound 207 may received by sound input element 202 as an electrical signal.

As shown in FIG. 2A, electrical signal 222 is output by sound input element 202 to an electronics module 204. Electronics module 204 is configured to convert electrical signal 222 into an adjusted electrical signal 224. As described below in more detail, electronics module 204 may include a sound processor, control electronics, transducer drive components, and a variety of other elements.

As shown in FIG. 2A, a transducer 206 receives adjusted electrical signal 224 and generates a mechanical output force that is delivered to the skull of the recipient via an anchor system 208 coupled to bone conduction device 200. Delivery of this output force causes one or more of motion or vibration of the recipients skull, thereby activating the hair cells in the cochlea via cochlea fluid motion.

FIG. 2A also illustrates a power module 210. Power module 210 provides electrical power to one or more components of bone conduction device 200. For ease of illustration, power module 210 has been shown connected only to interface module 212 and electronics module 204. However, it should be appreciated that power module 210 may be used to supply power to any electrically powered circuits/components of bone conduction device 200.

Bone conduction device 200 further includes an interface module 212 that allows the recipient to interact with device 200. For example, interface module 212 may allow the recipient to adjust the volume, alter the speech processing strategies, power on/off the device, etc. Interface module 212 communicates with electronics module 204 via signal line 228.

In the embodiment illustrated in FIG. 2A, sound pickup device 202, electronics module 204, transducer 206, power module 210 and interface module 212 have all been shown as integrated in a single housing, referred to as housing 225. However, it should be appreciated that in certain embodiments of the present invention, one or more of the illustrated components may be housed in separate or different housings. Similarly, it should also be appreciated that in such embodiments, direct connections between the various modules and devices are not necessary and that the components may communicate, for example, via wireless connections.

Figure 2B:
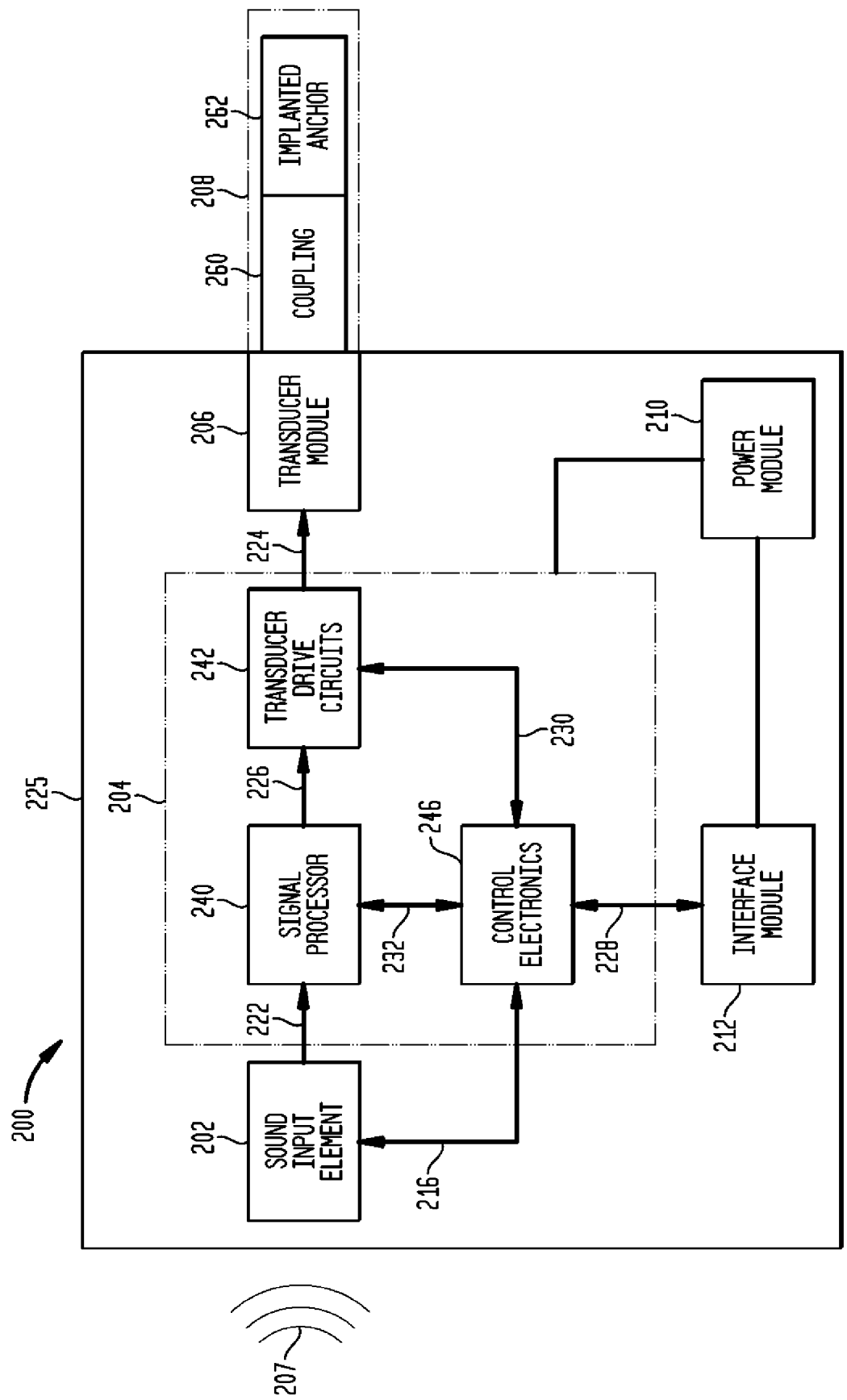
FIG. 2B is detailed functional block diagram of the bone conduction device illustrated in FIG. 2A.

FIG. 2B provides a more detailed view of bone conduction device 200 of FIG. 2A. In the illustrated embodiment, electronics module 204 comprises a sound processor 240, transducer drive components 242 and control electronics 246. As explained above, in certain embodiments sound input element 202 comprises a microphone configured to convert a received acoustic signal into electrical signal 222. In other embodiments, as detailed below, sound input element 202 receives sound 207 as an electrical signal.

In embodiments of the present invention, electrical signal 222 is output from sound input element 202 to sound processor 240. Sound processor 240 uses one or more of a plurality of techniques to selectively process, amplify and/or filter electrical signal 222 to generate a processed signal 224A. In certain embodiments, sound processor 240 may comprise substantially the same sound processor as is used in an air conduction hearing aid. In further embodiments, sound processor 240 comprises a digital signal processor.

Processed signal 226A is provided to transducer drive components 242. Transducer drive components 242 output a drive signal 224B, to transducer 206. Based on drive signal 224B, transducer 206 provides the output force to the skull of the recipient.

For ease of description the electrical signal supplied by transducer drive components 242 to transducer 206 has been referred to as drive signal 224B. However, it should be appreciated that processed signal 224B may comprise an unmodified version of processed signal 224A.

As noted above, transducer 206 generates an output force to the skull of the recipient via anchor system 208. As shown in FIG. 2B, anchor system 208 comprises a coupling 260 and an implanted anchor 262. Coupling 260 may be attached to one or more of transducer 206 or housing 225. For example, in certain embodiments, coupling 260 is attached to transducer 206 and vibration is applied directly thereto. In other embodiments, coupling 260 is attached to housing 225 and vibration is applied from transducer 206 through housing 225.

As shown in FIG. 2B, coupling 260 is coupled to an anchor implanted in the recipient, referred to as implanted anchor 262. As explained with reference to FIG. 3, implanted anchor 262 provides an element that transfers the vibration from coupling 260 to the skull of the recipient.

As noted above, a recipient may control various functions of the device via interface module 212. Interface module 212 includes one or more components that allow the recipient to provide inputs to, or receive information from, elements of bone conduction device 200.

As shown, control electronics 246 may be connected to one or more of interface module 212, sound pickup device 202, sound processor 240 and/or transducer drive components 242. In embodiments of the present invention, based on inputs received at interface module 212, control electronics 246 may provide instructions to, or request information from, other components of bone conduction device 200. In certain embodiments, in the absence of user inputs, control electronics 246 control the operation of bone conduction device 200.

Figure 3:
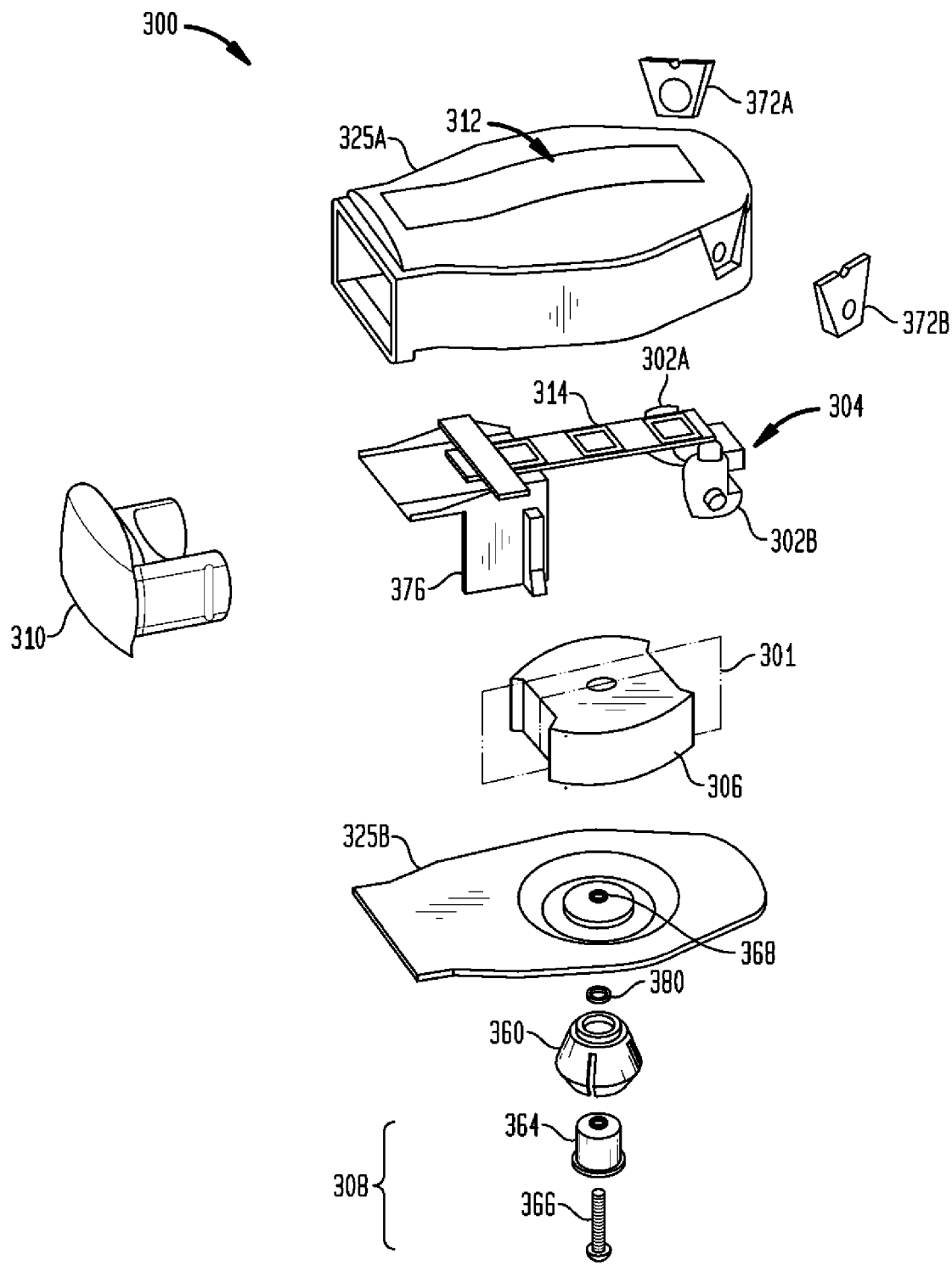
FIG. 3 is an exploded view of an embodiment of a bone conduction device in accordance with one embodiment of FIG. 2B.

FIG. 3 illustrates an exploded view of one embodiment of bone conduction 200 of FIGS. 2A and 2B, referred to herein as bone conduction device 300. As shown, bone conduction device 300 comprises an embodiment of electronics module 204, referred to as electronics module 304. As explained above, included within electronics module 304 are a sound processor, transducer drive components and control electronics. For ease of illustration, these components have not been illustrated in FIG. 3.

In the illustrated embodiment, electronics module 304 includes a printed circuit board 314 (PCB) to electrically connect and mechanically support the components of electronics module 304. Attached to PCB 314 are one or more sound input elements, shown as microphones 302 to receive a sound.

In the illustrated embodiment, bone conduction device 300 further comprises battery shoe 310 for supplying power to components of device 300. Battery shoe 310 may include one or more batteries. In certain embodiments, PCB 314 is attached to a connector 376. Connector 376 is configured to mate with battery shoe 310. In certain embodiments, connector 376 and battery shoe 310 may be releasably snap-locked to one another. Furthermore, in such embodiments, one or more battery connects (not shown) are disposed in connector 376 to electrically connect battery shoe 310 with electronics module 304.

In the embodiment illustrated in FIG. 3, bone conduction device 300 further includes a two-part housing 325, comprising first housing portion 325A and second housing portion 325B. Housing portions 325 are configured to mate with one another to substantially seal bone conduction device 300.

In the embodiment of FIG. 3, first housing portion 325A has an opening therein for receiving battery shoe 310. In such embodiments, battery shoe protrudes through first housing portion 325A and may be removed or inserted by the recipient. Also in the illustrated embodiment, microphone covers 372 are releasably attached to first housing portion 325A. Microphone covers 372 provide a barrier over microphones 302 to protect microphones 302 from dust, dirt or other debris.

Bone conduction device 300 further includes an embodiment of interface module 212, referred to herein as interface module 312. Interface module 312 is configured to provide or receive user inputs from the recipient.

Also as shown in FIG. 3, bone conduction device 300 comprises an embodiment of transducer 206, referred to as transducer 306. Transducer 306 generates an output force that causes movement of the cochlea fluid so that a sound may be perceived by the recipient. The output force may result in mechanical vibration of the recipient's skull, or in physical movement of the skull about the neck of the recipient. As noted above, in certain embodiments, bone conduction device 300 delivers the output force to the skull of the recipient via an anchor system 308. Anchor system 308 comprises a coupling 360 and implanted anchor 362. In the embodiment illustrated in FIG. 3, coupling 360 is configured to be attached to second housing portion 325B. As such, in this embodiment, vibration from transducer 306 is provided to coupling 360 through housing 325B. In the embodiment shown in FIG. 3, an opening 368 is provided in second housing portion 325B. A screw (not shown) may be inserted through opening 368 to attach transducer 306 to coupling 360. In such embodiments, an O-ring 380 may be provided to seal opening 368 around the screw.

As noted above, anchor system 308 includes implanted anchor 362. Implanted anchor 362 comprises a bone screw 366 implanted in the skull of the recipient and an abutment 364. In an implanted configuration, screw 366 protrudes from the recipient's skull through the skin. Abutment 364 is attached to screw 366 above the recipient's skin. In other embodiments, abutment 364 and screw 366 may be integrated into a single implantable component. Coupling 360 is configured to be releasably attached to abutment 364 to create a vibratory pathway between transducer 306 and the skull of the recipient.

In alternative embodiments of the present invention, bone conduction device 300 may comprise one or more additional sound input element. For example, bone conduction device 300 may comprises an electrical input 316. In such embodiments, the electrical input is configured to connect device 300 to external equipment and receive an electrical sound signal directly therefrom. Electrical input 316 may permit bone conduction device 300 to be connected to, for example, FM hearing systems, MP3 players, televisions, mobile phones, etc.

In still other embodiments, a further sound input element in the form of a telecoil 318 may be integrated in, or connected to, bone conduction device 300. Telecoil 318 permits bone conduction device 300 to receive input signals from, for example, a telephone or other similar device.

FIG. 4 illustrates the conversion of an input acoustic sound signal into a mechanical force for delivery to the recipient's skull in accordance with embodiments of bone conduction device 300. At block 402, bone conduction device 300 receives an acoustic sound signal. In certain embodiments, the acoustic sound signal is received via microphones 302. In other embodiments, the input sound is received via an electrical input. In still other embodiments, a telecoil integrated in, or connected to, bone conduction device 300 may be used to receive the acoustic sound signal.

At block 404, the acoustic sound signal received by bone conduction device 300 is processed by the speech processor in electronics module 304. As explained above, the speech processor may be similar to speech processors used in acoustic hearing aids. In such embodiments, speech processor may selectively amplify, filter and/or modify acoustic sound signal. For example, speech processor may be used to eliminate background or other unwanted noise signals received by bone conduction device 300.

At block 406, the processed sound signal is provided to transducer 306 as an electrical signal. At block 408, transducer 306 converts the electrical signal into a mechanical force configured to be delivered to the recipient's skull via anchor system 308 so as to illicit a hearing perception of the acoustic sound signal.

FIG. 5 illustrates one embodiment of block 408 of FIG. 4 in accordance with certain embodiments of the present invention. At block 504, the electrical signal is applied to at least one piezoelectric element. As explained above, the piezoelectric element is configured to deform in response to the application of the electrical signal thereto. Piezoelectric elements that may be used in embodiments of the present invention may comprise, for example, piezoelectric crystals, piezoelectric ceramics, or some other material exhibiting a deformation in response to an applied electrical signal. Exemplary piezoelectric crystals include quartz (SiO2), Berlinite (AlPO4), Gallium orthophosphate (GaPO4) and Tourmaline. Exemplary piezoelectric ceramics include barium titanate (BaTiO30), lead zirconate titanate (PZT), or zirconium (Zr).

Some piezoelectric materials, such as PZT, are polarized materials. When an electric field is applied across these materials, the polarized molecules align themselves with the electric field, resulting in induced dipoles within the molecular or crystal structure of the material. This alignment of molecules causes the deformation of the material under an applied electric field.

Returning to the embodiments illustrated in FIG. 5, at block 506 the transducer uses the deformation of the piezoelectric element to generate a stroke for the transducer that exceeds the deformation of the piezoelectric element. As explained in detail below, transducer may comprise one or more components configured to generate the transducer stroke based on the deformation of the piezoelectric element. At block 508, the mechanical force for delivery to the recipient's skull is generated based on the transducer stroke applied to the attached mass 560. The force applied is simply the mass times the acceleration which is applied by the transducer.

FIGS. 6A and 6B are simplified schematic diagrams illustrating embodiments of transducer 306 of FIG. 3, referred to herein as transducer 606. As shown, transducer 606 comprises a mechanical amplifier 620, piezoelectric element 640 and a mass 650.

In the embodiments of FIGS. 6A and 6B, mechanical amplifier 620 converts a deformation of piezoelectric element 640 into a mechanical deflection of one or portions of mechanical amplifier 620. The collective deflection of these portions exceeds the magnitude of the deformation of piezoelectric element 640. In these embodiments, the output stroke for transducer 606 comprises this collective deflection of the portions of mechanical amplifier 620.

In the illustrative embodiments of FIGS. 6A-6E piezoelectric element 640 comprises a plurality of layers of stacked piezoelectric material, referred to herein as a piezoelectric stack 640. For example, in some embodiments, piezoelectric stack 640 comprises a plurality of stacked PZT layers.

As noted above, in the embodiments of FIGS. 6A and 6B, a mechanical amplifier 620 is provided to mechanically amplify a deformation of piezoelectric stack 640. As shown in FIGS. 6A and 6B, mechanical amplifier 620 comprises two endplates 624 each coupled to a separate end of piezoelectric stack 640. Mechanical amplifier 620 further comprises opposing hinge arms 622, 628, extending between endplates 624. Arms 622 and 628 are positioned on opposing sides of piezoelectric element 640. In the embodiments of FIGS. 6A and 6B, each opposing arm 622, 628, and piezoelectric stack 640 define a frusto-conical shape there between. In these embodiments, each arm 622, 628 has a portion 626 spaced from piezoelectric element 640 by a distance that exceeds the remainder of each of arms 622, 628.

FIG. 6A illustrates the configuration of transducer 606 prior to application of an application signal to piezoelectric stack 640, while FIG. 6B illustrates the configuration of transducer 606 following application of the electrical signal to stack 640. Prior to application of the electrical signal, portions 626 of arms 622, 628 are each spaced a first distance from piezoelectric element 640. Following application of the electrical signal, piezoelectric stack 640 deforms along an axis extending there through substantially parallel to portions 626. This axis is illustrated as axis 611. As shown, piezoelectric stack 640 deforms by contracting along axis 611. This contraction of piezoelectric stack 640 along axis 611 causes portions 626 to deflect outwards from piezoelectric stack 640 along an axis substantially perpendicular to the axis of contraction, illustrated as axis 613 in FIGS. 6A and 6B. The magnitude of the deflection of each portion 626 is illustrated in FIGS. 6A and 6B as deflection 630.

In these embodiments, the magnitude of the collective deflection of portions 626 is referred to as the stroke of transducer 606. Due to the configuration of opposing arms 622, 628, the magnitude of the collective deflections 630 exceeds the magnitude of the contraction of piezoelectric stack 640 along axis 611. As would be appreciated, the larger the collective deflection of portions 626, the greater the stroke of transducer 606.

As noted above, transducer 606 includes a mass 650. When portions 626 deflect away from piezoelectric element 640, mass 650 is caused to move in proportion to the transducer stroke. This motion of mass 650 results in the generation of a mechanical force which may be output by transducer 606. In the embodiment of FIG. 6B, the generated mechanical force is illustrated by force arrow 625.

In the illustrated embodiment, hinge arm 622, 628 are utilized to output the mechanical force to, for example, a coupling described above with reference to FIG. 3. Hinge arms 622, 638 a sufficiently rigid material so as to output the mechanical force, but have dimensions, thickness and or other material properties that permit the deflection of portions 626 discussed above. Hinge arms 622, 628, and mechanical amplifier in general, may comprise a variety of materials. In certain embodiments, mechanical amplifier 620 is tungsten. In other embodiments, mechanical amplifier 620 is stainless steel.

Mechanical amplifier 620 may comprise a single unitary piece. In other embodiments, mechanical amplifier 620 may comprise two or more components.

FIG. 6C is a cross-sectional view of one exemplary embodiment of transducer 306, taken along cross-sectional plane 301 of FIG. 3, referred to herein as transducer 606. As noted above, transducer 606 comprises a piezoelectric element 640, mechanical amplifier 620 and mass 650. Mechanical amplifier similarly comprises endplates 624, arms 622, 628 and portions 626. In the illustrative embodiment, endplate 624B is attached to an end of piezoelectric stack 640. Endplate 624A is coupled to piezoelectric stack 640 via a preloading element 638. Preloading element 638 is designed to exert a compressive force on piezoelectric stack 640 while positioned within mechanical amplifier 620. This compressive force is applied to piezoelectric stack 640 due to the material property of piezoelectric stack 640. In these embodiments, piezoelectric stack 640 has a superior response to an applied electrical when the stack is placed under compression as compared to when the stack is under tensile forces. As such, in these embodiments, piezoelectric stack 640 is placed under the compressive force so that adequate expansion and contraction of piezoelectric stack 640 will occur when the electrical signal is applied thereto. It should be appreciated that in other embodiments mechanical amplifier 620 may be designed to exert the desired constant on piezoelectric stack 640 without preloading element 638.

As discussed above with reference to FIGS. 6A and 6B, mass 650 may be attached to portion 626A of arm 622. As shown in FIG. 6C, portion 626A is attached to mass 650 via attachment screw 646. Portion 626B of arm 628 is attached to a coupling 670 via coupling screw 672. As explained above with reference to FIG. 3, a coupling, such as coupling 670, may be attached to an anchor implanted in the recipient.

As noted, when an electrical signal is applied to piezoelectric stack 640, portions 626 deflect away from piezoelectric stack 640 along axis 613. In this illustrative embodiment, axis 613 is substantially perpendicular to the recipient's skull. As such, portion 626B deflects toward the recipient, while portion 626A deflects away from the recipient. As noted above, the magnitude of this collective deflection, referred to as the stroke of transducer 606, causes motion of mass 650. This motion in turn generates a mechanical force. This mechanical force may be output to coupling 670 and relayed to the anchor implanted in the recipient.

Figure 6D:
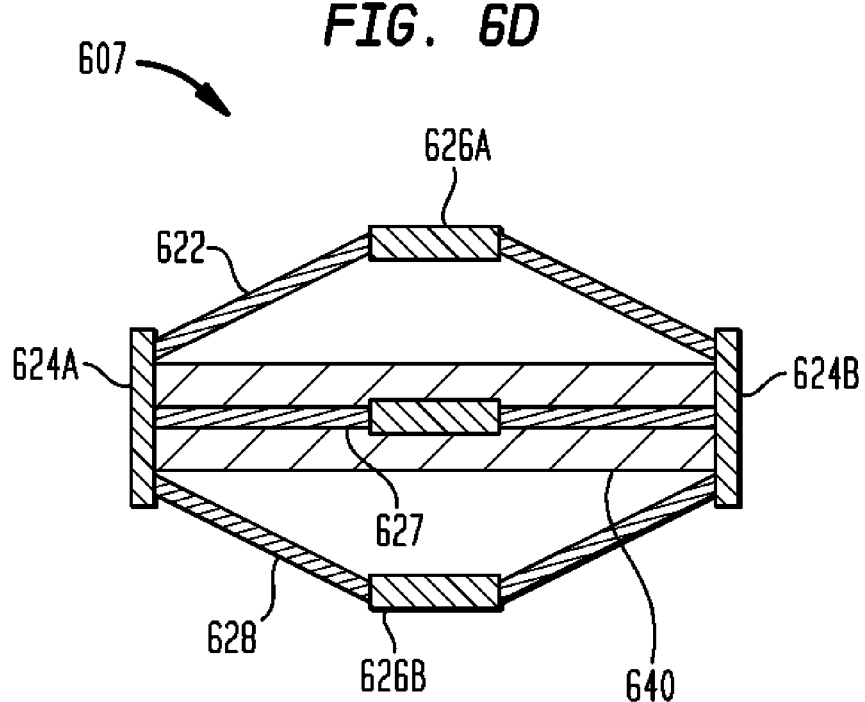
FIG. 6D is a simplified schematic diagram illustrating embodiments of transducer 306 of FIG. 3.

FIG. 6D illustrates an alternative embodiment of the present invention. In this embodiment, a mechanical amplifier 607 is provided to mechanically amplify a deformation of piezoelectric stack 640. Similar to the embodiments described above with reference to FIGS. 6A and 6B, mechanical amplifier 607 comprises two endplates 624 each coupled to a separate end of piezoelectric stack 640, and opposing hinge arms 622, 628 extending between endplates 624. Mechanical amplifier may comprise a second pair of opposing hinge arms. These second pair of hinge arms, shown by hinge arm 627 in FIG. 6D, may be positioned, for example, orthogonal to or parallel to, opposing hinge arms 622, 628. In the illustrative embodiment of FIG. 6D, the second pair of hinge arms 627 are positioned orthogonal to opposing hinge arms 622, 628. Opposing hinge arms 627 are similar to the previously described hinge arms and are positioned on opposing sides of piezoelectric element 640. Each opposing arm 627 and piezoelectric stack 640 define a frusto-conical shape there between. For ease of illustration, only one hinge arm 627 has been shown. In certain embodiments, hinge arms 627 may comprise the same or different material, height, etc. as the other set of hinge arms 622, 628. As such, hinge arms 627 may have the same or different response upon deformation of piezoelectric stack 640 as hinge arms 622, 628.

Figure 6E:
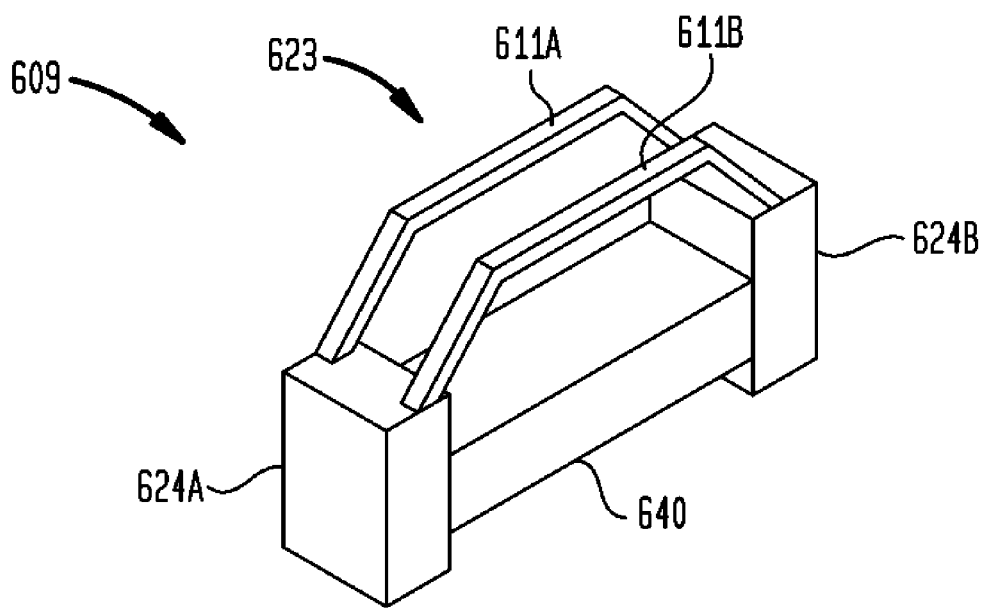
FIG. 6E is a simplified schematic diagram illustrating embodiments of transducer 306 of FIG. 3.

FIG. 6E illustrates another embodiment of the present invention. In this embodiment, a mechanical amplifier 609 is provided to mechanically amplify a deformation of piezoelectric stack 640. Similar to the embodiments described above with reference to FIGS. 6A and 6B, mechanical amplifier 609 comprises two endplates 624 each coupled to a separate end of piezoelectric stack 640, and opposing hinge arms extending between endplates 624. For ease of description, only one hinge arm 623 has been illustrated.

In the illustrative embodiment of FIG. 6E, hinge arm 623 comprises a split hinge arm having two arms 611. These arms 611 may comprise the same or different material. Likewise, arms 611 may be substantially parallel to one another, or they may be offset from one another. In operation, two different masses may be coupled to each arm 611 so that two different resonant frequencies may be produced.

In other embodiments, a transducer in accordance with embodiments of the present invention may use opposing mechanical amplifiers to amplify the deformation of a piezoelectric element. For example, two mechanical amplifiers, such as those described above in any of the embodiments of FIGS. 6A-6E, would be used to amplify the deformation of the piezoelectric element. In certain such embodiments, the two mechanical amplifiers would be positioned on opposite sides of the piezoelectric element to amplify the deformation.

FIGS. 7A and 7B are schematic diagrams of transducer 306, referred to herein as transducer 706, in accordance with alternative embodiments of the present invention. In the embodiments illustrated in FIGS. 7A and 7B, transducer 706 comprises endplates 728, first and second piezoelectric elements 742, 744, respectively, and mass 750.

In the embodiments of FIGS. 7A and 7B, first and second piezoelectric elements 742, 744, each comprise a polarized piezoelectric disk. Piezoelectric disk 742, 744 are each configured to deform at their geometric center in response to the application of an electrical signal thereto. In other words, piezoelectric disks 742, 744 each respond to the application of an electrical signal by buckling at its geometric center.

As shown in FIGS. 7A and 7B, first and second piezoelectric disks 742, 744 extend between endplates 728. Piezoelectric disks 742, 744 are adjacent and laterally spaced and have their polarization directions facing each other. As shown in FIG. 7B, due to these opposing polarization directions, simultaneous delivery of an electrical signal to disks 742, 744 will cause each disk to deform in substantially opposite directions. The disks are positioned such that the approximate geometric center of each disk will deform in a direction that substantially away from the opposing disk.

FIG. 7A illustrates the configuration of transducer 706 prior to application of an application signal to piezoelectric disks 742, 744, while FIG. 7B illustrates the configuration of transducer 706 following application of the electrical signal to stack 640. Prior to application of the electrical signal, the geometric centers of piezoelectric disks 742, 744 are spaced a first distance from one another. Following application of the electrical signal, piezoelectric disks 742, 744 deform at their geometric center. The magnitude of deformation of each disk is shown as deformation 730 in FIGS. 7A and 7B.

In these embodiments, the magnitude of the collective deformation of the geometric centers of disks 742, 744 is referred to as the stroke of transducer 706. Due to the use of two piezoelectric disks 742, 7444, the magnitude of the collective deformation 730 exceeds the magnitude of the deformation of a single piezoelectric element. As would be appreciated, the larger the collective deformation of disks 742, 744, the greater the stroke of transducer 706.

As noted above, transducer 706 includes a mass 750. When the geometric centers of disks 742, 744 deform, mass 750 is caused to move relative to the deformation. This motion of mass 750 results in the generation of a mechanical force which is output by transducer 706. In the embodiment of FIG. 7B, the generated mechanical force is illustrated by force arrow 725.

Disks 742 and 744 are shown in FIGS. 7A and 7B as separated by endplates 728. However, it should be appreciated that in other embodiments, endplates 738 may be eliminated. For example, in such alternative embodiments, disks 742 and 744 may be separated by O-rings, stacked leaf-springs etc.

As described in more detail below, in certain embodiments a disk 742 comprises two or more layers of piezoelectric material bound to an intervening thin metal plate. The polarization direction of the piezoelectric elements bound to the metal disk are arranged to create a larger deflection at the center of the plate. Preferably the polarization directions of the piezoelectric materials are opposed to each other. As a result of the application of an electrical signal to the disk 742, the piezoelectric elements deform. The central plate forms one terminal and the outer contacts form the other terminal for the electrical connection.

FIGS. 8A and 8B are schematic diagrams of transducer 306, referred to herein as transducer 806, in accordance with other embodiments of the present invention. In the embodiments illustrated in FIGS. 8A and 8B, transducer 806 comprises endplates 828, first and second piezoelectric elements 842, 844 respectively, and mass 850.

In the embodiments of FIGS. 8A and 8B, first and second piezoelectric elements 842, 844 each comprise a layer, or two or more layers as previously described, of piezoelectric material 846 boned to a shim 848. Shims 848 may be a material that provides rigidity to piezoelectric elements 842, 844, but that also do not interfere with the piezoelectric characteristics of layers 846. Piezoelectric elements 842, 844 are each configured to deform at their geometric center in response to an applied electrical signal. In other words, piezoelectric elements 842, 844 each respond to the application of an electrical signal by buckling at its center.

As shown in FIGS. 8A and 8B, first and second piezoelectric elements 842, 844 extend between endplates 828. Piezoelectric elements 842, 844 are adjacent and laterally spaced. The polarization directions of piezoelectric layers 848 are facing each other. As shown in FIG. 8B, due to these opposing polarization directions, simultaneous delivery of an electrical signal piezoelectric elements 842, 844 will cause layers 848 to deform in substantially opposite directions.

FIG. 8A illustrates the configuration of transducer 806 prior to application of an application signal to piezoelectric elements 842, 844, while FIG. 8B illustrates the configuration of transducer 806 following application of the electrical signal to elements 842, 844. Prior to application of the electrical signal, the geometric centers of piezoelectric elements 842, 844 are spaced a first distance from one another. Following application of the electrical signal, piezoelectric layers 848 each deform at their geometric center. The magnitude of deformation of each layer is shown as deformation 830 in FIGS. 8A and 8B.

In these embodiments, the magnitude of the collective deformation of the geometric centers of piezoelectric elements 842, 844 is referred to as the stroke of transducer 806. Due to the use of two piezoelectric elements 842, 844, the magnitude of the collective deformation 830 exceeds the magnitude of the deformation of a single piezoelectric element. As would be appreciated, the larger the collective deformation of elements 842, 844, the greater the stroke of transducer 806.

As noted above, transducer 806 includes a mass 850. When the geometric centers of piezoelectric elements 842, 844 deform, mass 850 is caused to move relative to the deformation. This motion of mass 850 results in the generation of a mechanical force which is output by transducer 806. In the embodiment of FIG. 8B, the generated mechanical force is illustrated by force arrow 825.

Piezoelectric elements 842 and 844 are shown in FIGS. 8A and 8B as separated by endplates 828. However, it should be appreciated that in other embodiments, endplates 838 may be eliminated. For example, in such alternative embodiments, piezoelectric elements 842 and 844 may be separated by O-rings, stacked leaf-springs etc.

FIGS. 8A and 8B have been discussed herein with reference to one exemplary arrangement for piezoelectric elements 842, 844, namely a layer of piezoelectric material bonded to a shim. It should be appreciated that other embodiments are included within the scope of the present invention. For example, in some embodiments, the piezoelectric elements comprise a piezoelectric disk bonded to a shim. In other embodiments, the piezoelectric elements comprise multiple layers of piezoelectric material bonded to one or more shims. In such embodiments, the piezoelectric elements may comprise a piezoelectric buzzer.

FIGS. 9A and 9B are schematic diagrams of a still other embodiment of transducer 306 of FIG. 3, referred to as transducer 906. In these embodiments, a hydraulic amplifier is provided generate the transducer stroke.

As shown in FIGS. 9A and 9B, transducer 906 comprises a piezoelectric element 940, hydraulic amplifier 920 and a mass 950. Hydraulic amplifier 920 comprises a first flexible metallic membrane 962, a volume 970 of incompressible fluid 971, and a second metallic membrane 964. Fluid 971 is bounded by first and second membranes 962, 964, and a housing 968. A substantially larger volume of fluid 971 is adjacent membrane 962 than is adjacent membrane 964. Membranes 962, 964 have sufficient rigidity to bound volume 970, but are flexible enough to respond to additional forces exerted thereon.

In the illustrated embodiments, piezoelectric element 940 is positioned adjacent, and in contact with, first membrane 962. First membrane 962 adjoins volume 970. Second membrane 964 adjoins volume 970 approximate opposite to first membrane 962.

FIG. 9A illustrates the configuration of transducer 906 prior to application of an application signal to piezoelectric element 940, while FIG. 9B illustrates the configuration of transducer 906 following application of the electrical signal to piezoelectric element 940. As shown, application of the electrical signal to piezoelectric element 940 is causes piezoelectric element 940 to deform in the direction of first membrane 962. The deformation of piezoelectric element 940 exerts a force on membrane 962 in the direction of fluid 971. This force on fluid 971 decreases the volume 970, and increases the pressure of the volume 970. This increase in pressure exerts a corresponding force on opposing second membrane 964 which causes the geometric center of second membrane 964 to deflect away from fluid 971. The deflection of the geometric center of second membrane 964 is illustrated in FIGS. 9A and 9B as deflection 930.

In these embodiments, the magnitude of the deformation of the geometric center of second membrane 964 is referred to as the stroke of transducer 906. Due to decrease in the volume 970 of fluid 971 as the volume 970 approaches second membrane 964, a pressure exerted via first membrane 962 is amplified at second membrane 962.

As noted above, transducer 806 includes a mass 950. In the illustrated embodiment, mass 950 is attached to piezoelectric element 940. When piezoelectric element 940 deforms, mass 950 is caused to move relative to the deformation. This motion of mass 950 results in the generation of a mechanical force which may be output by transducer 906. In the embodiment of FIG. 8B, the generated mechanical force is illustrated by force arrow 925.

The use of piezoelectric transducers as described herein may provided certain advantages over conventional devices. For example, it should be appreciated that piezoelectric transducers in accordance with embodiments of the present invention are non-magnetic transducers.

The use of a non-magnetic transducer provides the ability to directly incorporate a telecoil into the bone conduction device. As described above, telecoils permit bone a conduction device to receive input signals from, for example, a telephone or other similar device. Conventional devices using a magnetic transducer require that the telecoil be positioned a sufficient distance from the transducer to avoid interference. This is generally accomplished by mounting the telecoil on a stick or shaft extending from the device. In embodiments of the present invention, because there is no interference between the piezoelectric transducer and the telecoil, there is no need for remote positioning of the telecoil. As such, the telecoil may be included, for example, in the same housing as the transducer.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

What is claimed is:

1. A bone conduction device for enhancing the hearing of a recipient, comprising:
    a sound input element configured to receive an acoustic sound signal;
    an electronics module configured to generate an electrical signal representing said acoustic sound signal; and
    a piezoelectric transducer comprising at least one piezoelectric element configured to deform along at least one axis in response to an application of said electrical signal thereto, said transducer configured to generate a transducer stroke based on said deformation, said transducer stroke having a magnitude that exceeds the magnitude of said deformation,
    wherein said transducer stroke is utilized to generate a mechanical force for delivery to the recipient's skull.

2. The device of claim 1, wherein said transducer comprises a mechanical amplifier coupled to said piezoelectric element configured to convert said deformation of said piezoelectric element into a deflection of one or portions of said mechanical amplifier that collectively exceed the magnitude of said deformation, wherein said collective deflection comprises said transducer stroke.

3. The device of claim 2, wherein said deformation of said piezoelectric element comprises expansion of said element along said at least one axis and contraction of said element along at least a second axis, and wherein said mechanical amplifier comprises:
    a first endplate coupled to a first end of said piezoelectric element;
    a second endplate coupled to a second end of said piezoelectric element; and
    a first pair of opposing hinge arms connecting said first and second endplates, wherein when said piezoelectric element contracts along said second axis, at least one portion of each of said arms deflect outwards from said element substantially along said at least one axis.

4. The device of claim 3, wherein said at least one portion of each of said arms is spaced from said piezoelectric element by a distance that exceeds the remainder of each of said arms.

5. The device of claim 3, wherein at least one of said first or second endplates are coupled to said stack via one or more preloading elements.

6. The device of claim 3, wherein said at least one piezoelectric element comprises a piezoelectric stack.

7. The device of claim 3, wherein said mechanical amplifier comprises a unitary component.

8. The device of claim 3, wherein said mechanical amplifier comprises two or more components.

9. The device of claim 1, wherein said transducer comprises:
    a second piezoelectric element adjacent to and laterally spaced from said at least one piezoelectric element, said first and second piezoelectric elements each configured to deform in substantially opposite directions relative to one another, thereby generating a combined deformation having a magnitude that exceeds the magnitude of the deformation of said at least one element, and wherein said combined deformation comprises said transducer stroke.

10. The device of claim 9, wherein said first and second elements deform at their geometric centers.

11. The device of claim 9, wherein the magnitude of said deformation of said second piezoelectric element is approximately the same as the magnitude of said deformation of said at least one piezoelectric element.

12. The device of claim 9, wherein said first and second piezoelectric elements each comprise a piezoelectric disk bender.

13. The device of claim 9, wherein said first and second piezoelectric elements each comprise a piezoelectric strip bender.

14. The device of claim 9, wherein said first and second piezoelectric elements each comprise:
    a piezoelectric material bonded to a shim component.

15. The device of claim 9, wherein said first and second piezoelectric elements each comprise a piezoelectric buzzer.

16. The device of claim 1, having a hydraulic amplifier to generate said transducer stroke comprising:
    a bounded volume of incompressible fluid;
    a first flexible metallic membrane positioned between and adjoining said at least one piezoelectric element and said volume;
    at least a second metallic membrane adjoining said volume approximate opposite to said first membrane; and
    wherein deformation of said piezoelectric element along said axis causes said first flexible membrane to increase the pressure of said volume so as to cause a deflection of said second membrane, and wherein the surface area of said fluid adjoining said second membrane is substantially less than the surface area of said fluid adjoining said second membrane such that the deflection of said second membrane exceeds the deformation of said piezoelectric element.

17. The device of claim 3, wherein said mechanical amplifier further comprises:
    a second pair of opposing hinge arms connecting said first and second endplates.

18. The device of claim 3, wherein said second pair of hinge arms orthogonal to said first pair of hinge arms.

19. The device of claim 3, wherein each hinge arm in said second pair of hinge arms is substantially parallel to a hinge arm in said first pair of hinge arms.

20. The device of claim 3, wherein each of said hinge arms comprises a split hinge arm.

21. A method for rehabilitating the hearing of a recipient with a bone conduction device, comprising:
    receiving an electrical representation of an acoustic sound signal;
    delivering said electrical representation to at least one piezoelectric element of a piezoelectric transducer so as to deform said element;
    generating, based on said deformation, a transducer stroke having a magnitude that exceeds the magnitude of said deformation; and
    generating a mechanical force from said transducer stroke, wherein said force is configured for delivery to the recipient's skull.

22. The method of claim 21, wherein said generating said transducer stroke having a magnitude that exceeds the magnitude of said deformation comprises:

mechanically amplifying said deformation of said piezoelectric element.

23. The method of claim 22, wherein said transducer comprises a mechanical amplifier coupled to said piezoelectric element, and wherein amplifying said deformation comprises:
converting said deformation of said piezoelectric element into a deflection of one or portions of said mechanical amplifier that collectively exceeds the magnitude of said deformation.

24. The method of claim 23, wherein said mechanical amplifier comprises: first and second endplates coupled to respective ends of said piezoelectric element, a pair of opposing hinge arms connecting said first and second endplates, wherein said transducer stroke comprises:
delivering said electrical signal to said least one piezoelectric element so as to cause said element to contract along at least one axis and to expand along at least a second axis; and
deflecting at least one portion of each of said opposing arms substantially along said at least second axis, the magnitude of said deflection of said portions collectively exceeding the magnitude of said contraction;
wherein said collective deflection comprises said transducer stroke.

25. The method of claim 24, wherein said at least one portion of each of said arms are spaced from said piezoelectric element by a distance that exceeds the remainder of each said arm.

26. The method of claim 21, wherein transducer comprises a second piezoelectric element adjacent to and laterally spaced from said at least one piezoelectric element, and wherein said generating said transducer stroke comprises:
deforming said second piezoelectric element in a direction that is substantially opposite said deformation of said at least one piezoelectric element, thereby generating a combined deformation having a magnitude that exceeds the magnitude of the deformation of said at least one element,
wherein said combined deformation comprises said transducer stroke.

27. The method of claim 21, wherein said transducer comprises a hydraulic amplifier having a bounded volume of incompressible fluid, a first flexible metallic membrane positioned between and adjoining said at least one piezoelectric element and said volume, and at least a second metallic adjoining said fluid approximate opposite to said first membrane, wherein generating said transducer stroke comprises:
deflecting said first membrane in response to said deformation so as to increase the pressure of said volume of fluid;
deflecting said second membrane in an amount that exceeds said deformation,
wherein said deflection of said second membrane comprises said transducer stroke.

* * * * *